United States Patent [19]

Grassmé et al.

[11] 4,039,812

[45] Aug. 2, 1977

[54] X-RAY DIAGNOSTIC APPARATUS

[75] Inventors: Ulrich Grassmé, Nurnberg; Eickhardt Söder, Erlangen, both of Germany

[73] Assignee: Siemens Aktiengesellschaft, Berlin & Munich, Germany

[21] Appl. No.: 631,154

[22] Filed: Nov. 11, 1975

Related U.S. Application Data

[63] Continuation-in-part of Ser. No. 482,840, June 5, 1974, abandoned.

[30] Foreign Application Priority Data

June 28, 1973 Germany ............................ 2333004

[51] Int. Cl.2 .......................... A61B 6/00; H05G 1/30

[52] U.S. Cl. .................................................... 250/413

[58] Field of Search ............... 250/416, 409, 413, 403, 250/408

[56] References Cited

U.S. PATENT DOCUMENTS 1,603,049 10/1926 Hall ..................................... 250/413

*Primary Examiner*—Alfred E. Smith

*Assistant Examiner*—T. N. Grigsby

*Attorney, Agent, or Firm*—Hill, Gross, Simpson, Van Santen, Steadman, Chiara & Simpson

[57] ABSTRACT

An X-ray diagnostic apparatus having an adjustable mAs-relay for determining the exposure time. The adjustable mAs-relay is used for determining the exposure time, wherein the X-ray tube voltage and the X-ray tube current are varied in conformance with the fluctuations of the voltage supply. An operational amplifier may be employed, whose characteristics may, in a simple manner, be coordinated with the desired cycle of the mAs-product, in dependence upon the voltage supply. Additional auxiliary components for the voltage supply correlation are not required in the inventive arrangement.

9 Claims, 3 Drawing Figures

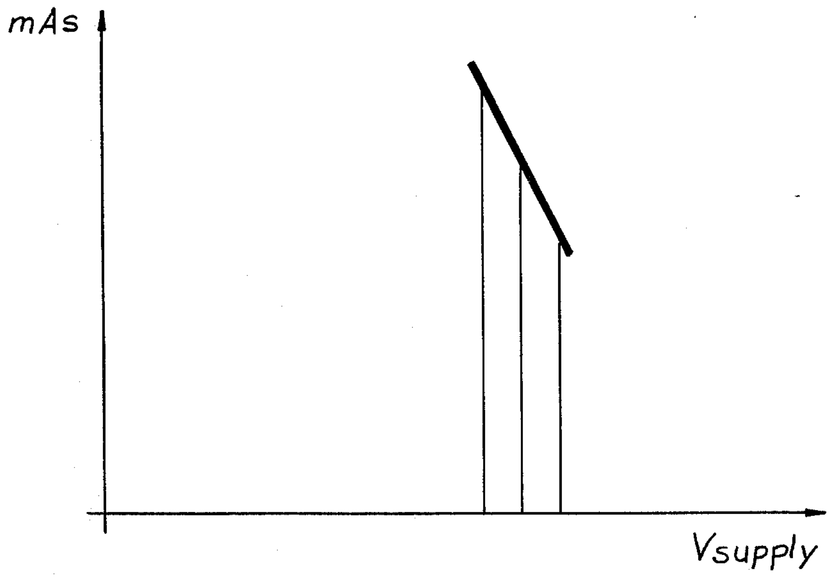
FIG. 2
FIG. 3
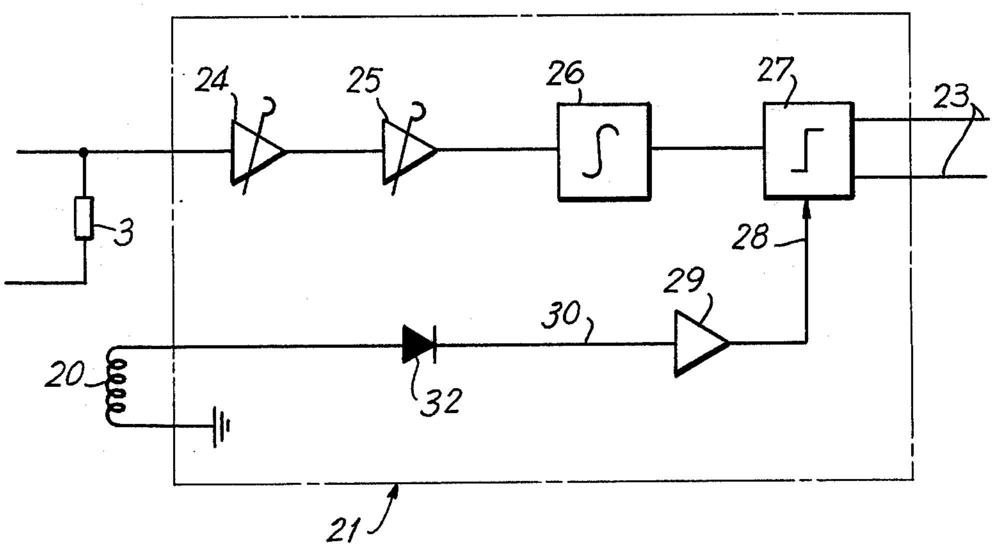

X-RAY DIAGNOSTIC APPARATUS

FIELD OF THE INVENTION

This application is a continuation-in-part application of Ser. No. 482,840; filed June 25, 1974 now abandoned.

The present invention relates to an X-ray diagnostic apparatus and, more particularly, to an apparatus having an adjustable mAs-relay for determining the exposure time.

DISCUSSION OF THE PRIOR ART

An X-ray diagnostic apparatus of the type mentioned has been described in German Laid-Open Patent Specification No. 1,922,398. In this X-ray diagnostic apparatus obtained optimally darkened X-ray images are obtained notwithstanding a fluctuating voltage supply, since the particularly adjusted mAs-product is automatically reduced with respect to a voltage supply which is increased relative to a reference value, and increased upon the supply voltage being lowered compared to the reference value. In order to coordinate the mAs-product with the X-ray tube voltage, there is provided a circuit arrangement including two direct-current sources having mutually opposed potentials, whose voltage cycle is so selected in dependence upon the voltage supply, whereby the X-ray dosage remains constant for a varying voltage supply. Both voltage sources are connected in series with each other, and are located in the input circuit of an oscillator element which, upon the attainment of a predetermined peak voltage, effects the termination of an exposure.

A disadvantage of the known circuit arrangement lies in its relatively large circuitry requirements, and in the only incomplete coordination between the mAs-product and the particular voltage supply.

SUMMARY OF THE INVENTION

Accordingly, it is an object of the present invention to provide an X-ray diagnostic apparatus of the type described which, in comparison with the state of the technology, provides a significantly simplified requirement for circuitry components, and facilitates an exact coordination of the particular mAs-product with the voltage supply.

The foregoing object is inventively attained by providing a novel and adjustable mAs-relay for determining the exposure time, wherein the X-ray tube voltage and the X-ray tube current are varied in conformance with the fluctuations of the voltage supply. For carrying out the invention object, there may be employed an operational amplifier, whose characteristics may, in a simple manner, be coordinated with the desired cycle of the mAs-product, in dependence upon the voltage supply. Additional auxiliary components for the voltage supply correlation are not required in the inventive arrangement.

Within the scope of the invention there may be connected in, ahead of an integrator for the X-ray tube current, an adjustable amplifier which is utilized for coordinating the mAs-product to the object being X-rayed, the constitution of the patient, the length of the particularly employed tube for the focusing of the X-ray beam, and the film sensitivity. The inventive X-ray diagnostic apparatus is particularly adapted for the preparation of dental X-ray exposures.

BRIEF DESCRIPTION OF THE DRAWINGS

Further advantages and details of the invention may now be ascertained form the following description of an exemplary embodiment thereof, taken in conjunction with the accompanying drawings; in which:

FIG. 2 graphically illustrates the required cycle of the mAs-product in dependence upon the voltage supply for maintaining constant the degree of film darkening; and FIG. 3 schematically illustrates the construction of the mAs-relay for the X-ray diagnostic apparatus of FIG 1.

DETAILED DESCRIPTION

Figure 1:
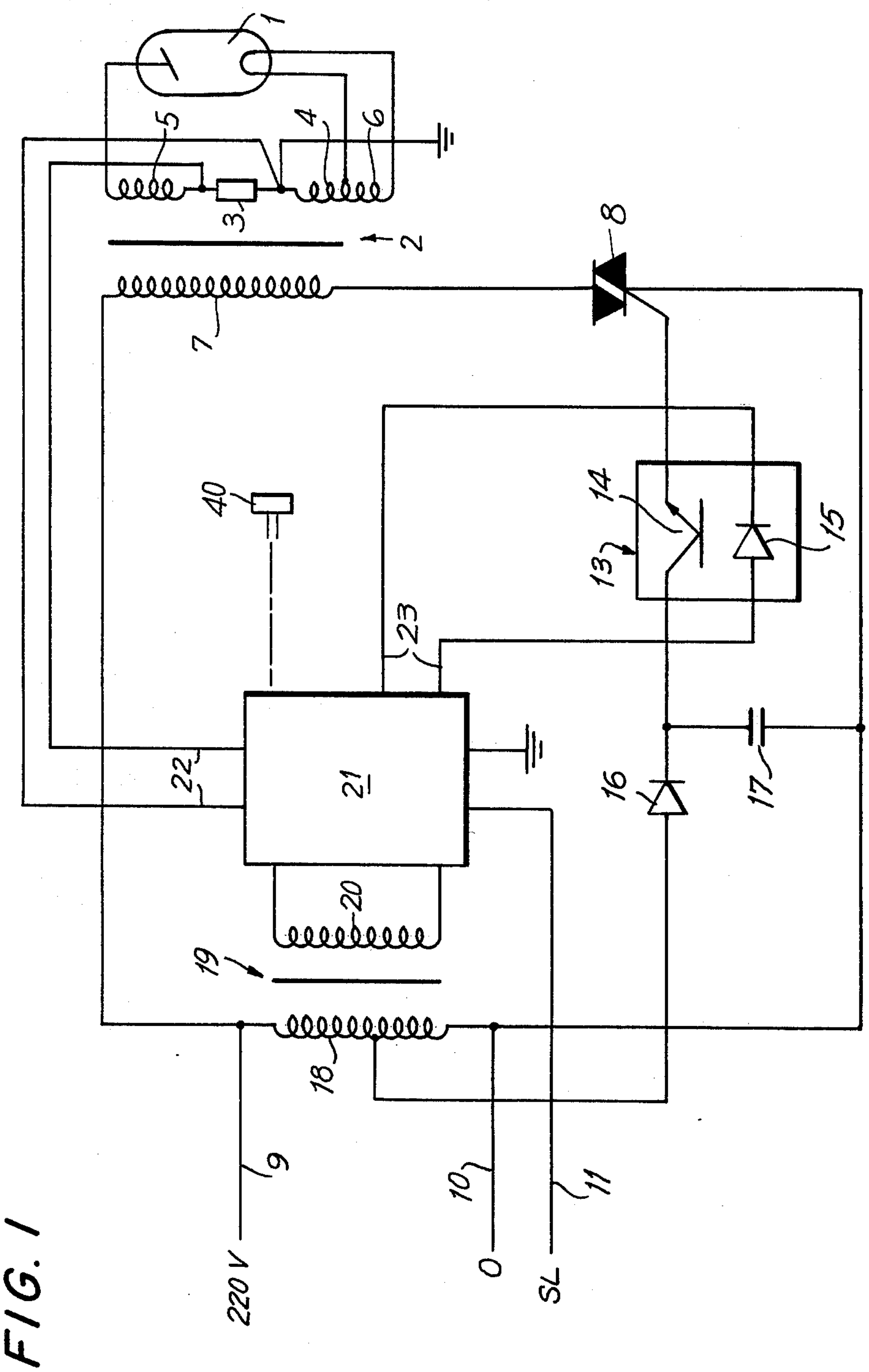
FIG. 1 shows a schematic circuit diagram for an X-ray diagnostic apparatus constructed in accordance with the present invention.

Referring now in detail to the drawing, in FIG. 1 there is illustrated an X-ray tube 1 which is powered from a high-voltage transformer 2. The high-voltage transformer 2 includes two secondary windings 4 and 5, which are connected in series with each other across a resistance 3, and which provide the high voltage for the X-ray tube 1, as well as a secondary winding 6 for the filament current of the X-ray tube 1. The primary winding 7 of the high-voltage transformer 2 is connectable to an alternating current supply through a triode 8. The connection may be effected by means of a suitable plug and socket arrangement. In view of the foregoing, there may, for example, be applied a voltage of 220 volts to a conduit 9, and a zero-potential to a conduit 10. A ground potential is always applied to conduit 11.

The triode 8 serves for the in-and-out switching of the X-ray tube 1 at its primary side. Its control electrode 12 is connected to an opto-coupler 13, the latter of which contains a photo-transistor 14 and a light-emitting diode 15. The phototransistor 14 is supplied with current from a direct-current source, the latter of which consists of a rectifier 16, a filter condensor 17, and a portion of the primary winding 18 of an auxiliary transformer 19.

The auxiliary transformer 19 supplies an mAs-relay 21 with the required operating voltages through the intermediary of a secondary winding 20, the relay receiving at its input 22 a signal which is tapped off from resistance 3, in effect, a signal which corresponds to the X-ray tube current. The light-emitting diode 15 is connected to the output 23 of mAs-relay 21.

With the commencement of an exposure through an exposure trigger device 40, the mAs-relay 21 generates, in a known manner, a signal at its output 23 which causes the light-emitting diode 15 to project a beam to the transistor 14. The transistor 14 is consequently switched into its low ohmic condition and transmits the direct-voltage delivered from the direct voltage sources 16, 17 and 18 to the ignition electrode 12 of the troide 8 so as to, in effect, cause the ignition of triode 8. The mAs-relay 21 integrates the X-ray tube current, and after the obtention of a predetermined mAs-product which provides for an optimum degree of film darkening, deactivates the light-emitting diode 15. Thereby the photo-transistor 14 is switched back into its high-ohmic condition, and terminates the ignition voltage at the ignition electrode 12. When the retaining current of the triode is consequently reduced, the triode 8 is cut off, and the X-ray tube 1 is again switched off.

The mAs-relay 21 in FIG. 1 contains means for varying the mAs-product in dependence upon the voltage supply. In FIG. 2 there is illustrated the required cycle or function of the mAs-products in dependence upon the voltage supply for obtaining a constant degree of film darkening. From FIG. 2 it may be ascertained that, with an increasing voltage supply and a thereby increasing X-ray dosage quantity, the mAs-product must reduce.

From FIG. 3 it may be ascertained that the mAs-relay 21 includes two amplifiers 24 and 25, each having adjustable amplifying characteristics, and an integrator 26 connected therewith. The output signal of the integrator 26 controls a trigger element 27, whose peak voltage or threshold is determined by the voltage at its input 28. A trigger of this type, whose threshold is variable through a signal, is described in Millman and Taub "Pulse, Digital, a Switching Waveforms", pages 465, 466; McGraw-Hill Inc. (1965) New York.

In essence, concerning element 27, this is merely a standard trigger element whose threshold is determined through the voltage at input 28. Since this voltage depends upon the voltage supply, the threshold is varied in dependence upon the supply votage, and thereby there is also effected a correlation of the adjusted mAs-product to the voltage supply. This trigger element, whose threshold is variable through a signal is known from the aforementioned publication of Millman and Taub, and is fully described on pages 465 and 466. In particular, in the last paragraph on page 465 a circuit arrangement is described in which the threshold voltage depends upon the intensity of a supplied current (Example $I_{GC}$). Element 27 may be constituted of a trigger of the type described in this publication. The voltage at input 28 is supplied by an amplifier 29, having linear characteristics as in FIG. 2, whose input conduit 30 receives a signal corresponding to the actual value of the voltage supply, and which is tapped off from the transformer winding 20. The amplifier 29 is an ordinary amplifier as described, for example, as disclosed in Millman and Taub, supra, on pages 23 and 24 (FIG. 1-19). The input voltage of this amplifier may be delivered from the winding 20 so as to provide rectification preceding the amplification. This is provided for by the positioning of a rectifier 32 in the input conduit 32 intermediate the transformer winding 20 and the amplifier 29. The output current of the amplifier 29 may be transmitted directly to trigger 27.

The amplifier 24 serves for the coordinating of the mAs-relay with the particular exposure object, for example, a tooth which is to be filmed, and the particular constitution of the patient. The amplifier 25 serves for coordination of th X-ray cone length and of the film sensitivity. The output voltage of the integrator 26 is a measure for the integral of the X-ray tube current. After achieving predetermined mAs-product, the output voltage, and thereby the input voltage of the trigger element 27, reaches the peak voltage of the oscillator element, so as to cause the trigger element 27 to reverse and switch off the light-emitting diode and, consequently, deactivate the X-ray tube 1. The peak voltage thereby is determined by means of the amplifier 29. The amplifying characteristics of the amplifier extend linearly in correspondence with the curve of FIG. 2, in effect, meaning that the output voltage of amplifier 29 provides a measure of the required mAs-product for the particular voltage supply for an optimum degree of film darkening. The output voltage of the amplifier 29, and thereby the peak voltage of the trigger element 27, also vary with a changing voltage supply, so that the mAs-product is also correspondingly varied.

The invention object permits in a simple manner, through the utilization of an amplifier 29 with a sequence of the amplifying characteristics corresponding with that of the mAs-product in dependence of the supply votage, of the coordination with the particular voltage supply. This requires no means for voltage regulation and produces optimally darkened X-ray pictures. In particular, a single-chamber generator may be utilized for the preparation of the X-ray exposures.

While there has been shown what is considered to be the preferred embodiment of the invention, it will be obvious that modifications may be made which come within the scope of the disclosure of the specification.

What is claimed is:

1. In an X-ray diagnostic apparatus having an adjustable mAs-relay for determining the exposure time for an X-ray exposure; an X-ray having variable X-ray tube voltage and current in conformance with fluctuations of a voltage supply; control means for controlling said mAs-product in dependence upon said voltage supply for maintaining constant an X-ray dosage, said X-ray dosage being predetermined through preset values for said mAs-product and the X-ray tube voltage; said mAs-relay including an integrator for the X-ray tube current and a trigger element, said trigger element adapted to be reversed upon receiving a predeterimed peak integrator voltage so as to emanate a signal for terminating the X-ray exposure; and means for controlling said mAs-relay in dependence upon the voltage supply for varying the peak voltage, said controlling means including an amplifier having an input receiving a voltage corresponding to the voltage supply and having linear characteristics providing a predetermined output voltage at an output thereof, said trigger element being connected to the output of said amplifier for varying the mAs-product dependent upon the voltage supply, and an adjustable amplifier being connected to said integrator for coordinating said mAs-product with an exposure object.

2. In an X-ray diagnostic apparatus having an adjustable mAs-relay for determining the exposure time for an X-ray exposure; an X-ray tube having variable X-ray tube voltage and current in conformance with fluctuations of a voltage supply; control means for controlling said mAs-product in dependence upon said voltage supply for maintaining constant an X-ray dosage, said X-ray dosage being predetermined through preset values for said mAs-product and the X-ray tube voltage; said mAs-relay including an integrator for the X-ray tube current and a trigger element, said trigger element adapted to be reversed upon receiving a predetermined peak integrator voltage so as to emanate a signal for terminating the X-ray exposure; and means for controlling said mAs-relay in dependence upon the voltage supply for varying the peak voltage, said controlling means including an amplifier having an input receiving a voltage corresponding to the voltage supply and having linear characteristics providing a predetermined output voltage at an output thereof, said trigger element being connected to the output of said amplifier for varying the mAs-product dependent upon the voltage supply, and at least one adjustable amplifier being connected to said integrator for coordinating said mAs-product with the sensitivity of an X-ray film.

3. In an X-ray diagnostic apparatus having an adjustable mAs-relay for determining the exposure time for an X-ray exposure; an X-ray tube having variable X-ray tube voltage and current in conformance with fluctuations of a voltage supply; control means for controlling said mAs-product in dependence upon said voltage supply for maintaining constant an X-ray dosage, said X-ray dosage being predetermined through preset values for said mAs-product and the X-ray tube voltage; said mAs-relay including an integrator for the X-ray tube current and a trigger element, said trigger element adapted to be reversed upon receiving a predetermined peak integrator voltage so as to emanate a signal for terminating the X-ray exposure; and means for controlling said mAs-relay in dependence upon the voltage supply for varying the peak voltage, said controlling means including an amplifier having an input receiving a voltage corresponding to the voltage supply and having linear characteristics providing a predetermined output voltage at an output thereof, said trigger element being connected to the output of said amplifier for varying the mAs-product dependent upon the voltage supply, and at least one adjustable amplifier being connected to said integrator for coordinating said mAs-product with the length of the X-ray cone.

4. In an X-ray diagnostic apparatus having an adjustable mAs-relay for determining the exposure time for an X-ray exposure; an X-ray tube having variable X-ray tube voltage and current in conformance with fluctuations of a voltage supply; control means for controlling said mAs-product in dependence upon said voltage supply for maintaining constant an X-ray dosage, said X-ray dosage being predetermined through preset values for said mAs-product and the X-ray tube voltage; said mAs-relay including an integrator having an integrator input circuit for receiving an input voltage which is a function of the X-ray tube current of said X-ray tube, and having an integrator output circuit for supplying an integrator output voltage which is a measure of the integral of the X-ray tube current, and including a plural-voltage-responsive element having a first input connected with said integrator output circuit for receiving said integrator output voltage which is a measure of the integral of the X-ray tube current, having a second input, and having an exposure-controlling output circuit for controlling the time duration of the X-ray exposure; said control means including an input for receiving a supply-voltage-responsive signal corresponding to the actual value of the voltage supply and having an output for supplying an output control voltage which is a measure of the required mAs-product for the supply-voltage-responsive signal received at it input, the plural-voltage-responsive element having its second input connected to the output of said control means and being responsive to the output control voltage from said control means to vary the peak value of the integrator output voltage at its first input which is required to actuate said plural-voltage-responsive element to terminate an X-ray exposure, such required peak value of the integrator output voltage being increased for decreasing values of the supply voltage as represented by said supply-voltage-responsive signal, and decreasing with an increasing supply voltage as represented by said supply-voltage-responsive signal, so as to maintain substantially a constant X-ray dosage independent of fluctuations in the voltage supply.

5. An X-ray diagnostic apparatus as claimed in claim 4, with said integrator input circuit comprising an adjustable amplifier having an input for receiving an input voltage which is a function of the X-ray tube current and having an output connected with said integrator for coordinating said mAs-product with an exposure object.

6. An X-ray diagnostic apparatus as claimed in claim 4 with said integrator input circuit comprising at least one adjustable amplifier for receiving an input voltage which is a function of the X-ray tube current and having an output connected to said integrator for coordinating said mAs-product with the sensitivity of an X-ray film.

7. An X-ray diagnostic apparatus as claimed in claim 4, said integrator input circuit comprising at least one adjustable amplifier having its input connected for receiving an input voltage which is a function of the X-ray tube current and having is output connected to the integrator for coordinating said mAs-product with the length of the X-ray cone.

8. An X-ray diagnostic apparatus as claimed in claim 4 with said control means comprising an electronic amplifier with an input receiving said supply-voltage-responsive signal and with an output connected with said second input of said plural-voltage-responsive element.

9. An X-ray diagnostic apparatus as claimed in claim 8 with said plural-voltage-responsive element being a trigger element whose switching threshold is controlled by the voltage at the output of said electronic amplifier.

* * * * *